US005520668A

United States Patent [19]
Greff et al.

[11] Patent Number: 5,520,668
[45] Date of Patent: May 28, 1996

[54] MEDICAL SUCTION SYSTEM AND METHOD

[75] Inventors: Richard J. Greff, Yorba Linda, Calif.; Ed F. Nicolas, Metro Manila, Philippines

[73] Assignee: Stackhouse, Inc., Riverside, Calif.

[21] Appl. No.: 315,597

[22] Filed: Sep. 30, 1994

[51] Int. Cl.⁶ .................................................. A61M 1/00
[52] U.S. Cl. ............................................ 604/321; 604/319
[58] Field of Search ...................................... 604/319–321

[56] References Cited

U.S. PATENT DOCUMENTS

| 2,804,075 | 8/1957 | Borden . | |
|---|---|---|---|
| 3,012,322 | 12/1961 | Thompson . | |
| 4,294,251 | 10/1981 | Greenwald et al. . | |
| 4,957,492 | 9/1990 | McVay | 604/319 |
| 5,076,787 | 12/1991 | Overmyer . | |

*Primary Examiner*—Randall L. Green
*Assistant Examiner*—Mark O. Polutta
*Attorney, Agent, or Firm*—Richard L. Myers

[57] ABSTRACT

A surgical suction system and method includes a source of suction and a conduit having a distal end and a proximal end. At its distal end, the conduit has a diameter not greater than about ⅝ inch to provide limited access to the surgical site and an inside diameter not less than about ¼ inch to accommodate the bone fragments in the waste slurry. A coupling is provided for connecting the proximal end of the conduit to the suction source in order to provide suction at the distal end of the conduit at a velocity not less than about ninety miles per hour. A fluid containment vessel can be connected between the conduit and the source of suction to provide a liquid trap for the waste slurry passing along the conduit. An associated method includes the step of activating the suction source to provide suction at the distal end of the conduit with a velocity not less than ninety miles per hour.

8 Claims, 3 Drawing Sheets

Fig. 2

VELOCITY (MPH)
TUBING INSIDE DIAMETER (INCHES)

| VOLUME (CFM) | 1/10 | 1/4 | 3/8 | 1/2 | 7/8 | 1 |
|---|---|---|---|---|---|---|
| 2.5 | 520 | 85 | 50 | 22 | 65 | 5 |
| 5 | 1035 | 165 | 100 | 43 | 13 | 10 |
| 10 | 2070 | 335 | 200 | 85 | 25 | 20 |
| 15 | 3110 | 500 | 300 | 130 | 38 | 30 |
| 20 | 4150 | 670 | 400 | 170 | 50 | 40 |
| 25 | 5185 | 840 | 500 | 215 | 65 | 50 |
| 30 | 6220 | 1005 | 600 | 255 | 75 | 60 |
| 35 | 7260 | 1175 | 700 | 300 | 90 | 70 |
| 50 | 10310 | 1175 | 1000 | 425 | 125 | 100 |

MEDICAL SUCTION SYSTEM AND METHOD

BACKGROUND OF THE INVENTION

1. Field of the Invention

This invention relates generally to medical suction apparatus and more specifically to a suction apparatus which is adapted for the removal and processing of gasses, liquids and other debris from a surgical site.

2. Discussion of the Prior Art

Medical suction is commonly used for removing gasses and liquids from a surgical site to a remote location. The source of suction is positioned at this remote location and a suction tube typically extends between the source and the surgical site. In some cases, the material removed from the surgical site must be processed at the remote location in order to avoid contamination of the environment.

Suction requirements differ widely and vary, for example, with the size of the operative site and the nature of the material being removed. The availability and proximity of suction sources must also be considered along with their respective specifications for static suction, volume of movement, and filtration. The proximity of the suction source to the surgical site, and hence the length and size of the tubing extending therebetween, must also be considered.

Two types of suction sources are presently available in most operating rooms. The first is a smoke evacuator which is a portable, stand-alone device which removes surgical smoke from the operative site and filters that smoke prior to releasing clean air to the operating room. A surgical smoke evacuator typical of this type apparatus is disclosed and claimed by applicant in U.S. patent application Ser. No. 07/960,934, filed on Oct. 14, 1992 and entitled Surgical Smoke Evacuator.

This apparatus is used for processing surgical smoke which commonly results from laser and electrosurgical procedures. This smoke interferes with visualization of the operative site and may also be contaminated. Accordingly, it is desirable that the smoke be removed from proximity with the patient, the surgeon and the operative staff.

The smoke evacuators are typically provided with adjustments or settings which control the velocity of the suction. Static suction in a range of 70 to 100 inches of water are common. This suction is typically delivered through tubing having an inside diameter of a ⅞ inch. This large dimension presents no problem considering the size of the operative site commonly associated with this type of surgery.

Another type of suction source is even more commonly available in operating rooms. This source is typically referred to as "wall vacuum" and is usually accessed through ¼ inch tubing. Wall vacuum generates 200 or more inches of water suction, but at relatively low flow rates of only 1–2 cubic feet per minute.

In addressing suction requirements in an operating room, one must then consider the nature of the material to be removed from the surgical site. Fluid waste such as blood or irrigation fluids are commonly removed using the wall suction. The ¼ inch tubing draws fluid from the surgical site and through a fluid trap or canister which is positioned along the tubing between the suction source and the surgical site. This system is considered adequate for most surgical waste in a fluid, low viscous state.

The relatively low flow rates associated with wall suction have made it totally ineffective in removing waste containing any debris. Such waste is commonly associated with orthopedic revisions of hip and knee joints. In these cases, the waste typically contains a significant amount of blood clot, fine bone debris, adhesive and other solids. Any attempt to aspirate this waste using the wall vacuum causes the suction tubing to become clogged with a thick mass of debris suspended in blood and irrigation fluid. Blood adds significantly to the complexity of this waste slurry. Blood which is exposed to air and left in a low velocity or stagnant state, tends to clot. This of course, can increase the viscosity of the waste slurry over time.

Although smoke evacuators have not been intended to address either liquid or solid waste, various attempts have been made to adapt these instruments for this purpose. Smoke evacuators commonly include large tubes having a diameter such as ⅞ to one inch. A hand piece such as that disclosed and claimed by applicant in U.S. patent application Ser. No. 7/888,974 filed May 26, 1992 is commonly provided at the operative end of the long tube. Tubing of this size is not at all suitable for use in orthopedic revisions due to the small size of the surgical site. Also, the large tubing associated with smoke evacuators generates a relatively low velocity. Consequently, the large mass associated with the complex slurry mentioned above will not move up the tube. The small tubing sizes typically associated with wall vacuum tend to fill with the slurry which then becomes too viscous to move. The low volume of air flow commonly associated with the smaller tubing also contributes to this adverse condition.

Since the available suction sources in the operating room have all been deficient in removing blood clots and other solid debris, the surgeon and his assistants have been required to alter their surgical techniques where this type of waste develops. In many cases, the solid debris has been manually removed from the liquid which has then been addressed with sponges and other techniques for removing liquid waste.

SUMMARY OF THE INVENTION

A medical suction system in accordance with the present invention is adapted to accommodate waste materials that are viscous and semi-solid, as is the case with orthopedic revisions of the hip and knee joints. Such waste will commonly consist of blood, irrigation fluid (saline), shaved, drilled, chipped natural bone, and bone cement (polymethylmethacrylate) debris. The amounts of each constituent will vary considerably particularly in the case of blood which will typically be in different stages of clotting. The particle size of bone and bone cement will also vary.

A smoke evacuator is used in the best mode of the invention, but the connective tubing varies considerably from that designed for either the smoke evacuator or the wall vacuum. This tubing in a preferred embodiment includes a six to ten foot section of ⅞ inch diameter tubing such as that commonly provided with the smoke evacuator. At the operative end of this tubing, a length of distal tube is provided. This distal tube will typically have an inside diameter between ⅜ and ½ inch and a length, such a four feet, which is sufficient to deliver suction at a velocity of at least ninety miles per hour. Wall vacuum is not capable of achieving this velocity with any tube configuration. However, the greater power associated with the smoke evacuators appears to be able to support this criteria.

The tubing cross-sectional area is a critical factor which contributes significantly to the pressure drop in a suction system. Tubing length also has an effect on the pressure drop but this effect is generally secondary unless the tubing is extremely long. In accordance with the present invention, the distal tube is provided with a sufficiently small diameter that it can easily access smaller surgical sites such as those associated with orthopedic hip and knee revisions. The distal tube is also provided with a diameter which is sufficiently large to provide the desired velocity of flow and to accommodate the particle size of the solid and semi-solid components in the waste. Smooth bore couplings are provided where the distal tube joins to the larger tubing. The smooth inner bore couplings prevent debris deposition and potential clogging on the inside of the tubing surface.

The suction velocity provided by this system accommodates the size and configuration of semi-solid waste. Stasis and clogging in the suction tubing are inhibited as a result of the high velocity provided by the suction source and the cross-sectional area provided by the tubing.

One aspect the invention includes a method for evacuating a waste slurry from an orthopedic surgical site where the slurry includes blood clots and bone fragments. The method includes the steps of providing a suction source, a conduit, and a fluid containment vessel. The conduit is provided with a proximal end and a distal end, and has a distal end diameter not greater than about ⅝ inch in order to provide limited access to the surgical site. The conduit also has at its distal end an inside diameter not less than about ¼ inch in order to accommodate the blood clots and bone fragments of the waste slurry. The method also includes the step of connecting the proximal end of the conduit to receive the suction from the suction source. Activating the suction source then provides suction at the distal end of the conduit with a velocity not less than about ninety miles per hour. Moving the waste slurry into the distal end of the conduit and through the conduit toward the suction source enables the waste slurry to be collected in the fluid containment vessel.

In another aspect, the invention includes a surgical suction system adapted for use in removing the waste slurry from the orthopedic surgical site. This system includes a source of suction and a conduit having a proximal end and a distal end. At its distal end the conduit has diameter not greater than about ⅝ inch and an inside diameter not less than about ¼ inch. The system includes means for coupling the proximal end of the conduit to receive suction from the suction source and to provide suction at the distal end of the conduit with a velocity of not less than ninety miles per hour. A fluid collection vessel is connected to the conduit between the distal end of the conduit and the source of suction to collect the waste slurry passing along the conduit.

These and other features and advantages of the invention will become more apparent with a discussion of preferred embodiments and the best mode of the invention, and reference to the associated drawings.

DESCRIPTION OF THE DRAWINGS

FIG. 2 is a table illustrating suction velocities given flow volumes and tubing inside diameters;

Figure 1:
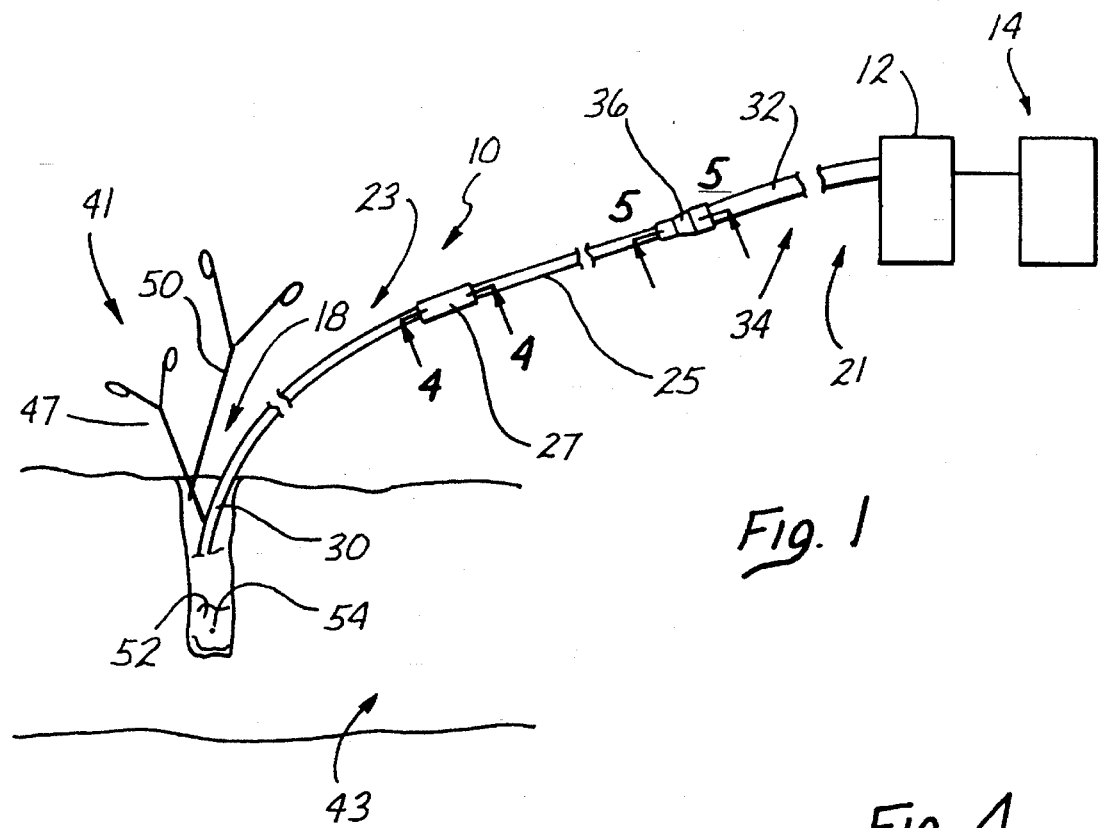
FIG. 1 is a perspective view of an orthopedic hip revision and a surgical suction system associated with the present invention.

DESCRIPTION OF PREFERRED
EMBODIMENTS AND BEST MODE OF THE
INVENTION

Suction is used to move gasses, liquids and solids from one location to another. In this process, a flow of fluid, such as air, is induced in proximity to an object to be moved. In a general sense, this flow consists of particles in motion. Where the suction is created by air, the particles include gas molecules and other fine particulates which are normally found in air. These particles have a certain velocity and therefore a momentum which is relied on to move the object of interest.

The momentum of any object is a function of its mass multiplied by the velocity. Accordingly, although the air particles may have very little mass, they nevertheless have a velocity and accordingly a momentum. When these particles strike the object to be moved, some of the momentum is imparted to the object which then begins to move with a velocity dependent on its mass.

In the case of suction which is used at a surgical site, the flow of air is brought into proximity with fluids and other debris which are then caused to move into a suction tube and along the tube to a containment vessel. When liquids, such as water and saline which are commonly used for aspiration, are the objects to be moved, the liquids are forced into the suction tubing and collected in a fluid canister by the lower pressure environment near the suction tip, as well as the momentum of the air particles.

Of particular interest to the present invention is the collection of complex waste which includes blood, and therefore tends to transition to a more solid state when brought into contact with air and maintained at a relatively low velocity. In some surgeries, this complex waste may include a high concentration of blood clot as well as other particulate matter such as bone debris resulting from shaved, drilled and chipped natural bone, as well as bone cement. This particulate waste can include bone chips as large as ¼ inch and may have a configuration that is more gelatinous than solid or liquid. This waste can be further complicated by the fact that the blood present in a high level of concentration may be in different stages of clotting.

This type of waste is commonly found in orthopedic applications associated with bone surgeries such as hip and knee replacements. It has been found that this type of waste, hereinafter referred to as a slurry, cannot be moved by air suction having a velocity less than about ninety miles per hour.

Suction at an orthopedic surgical site is limited by constraints as to the size of tubing which can be used in this environment. Generally, the surgical site is crowded with various instruments such as retractors, grippers and other devices for cutting, suturing, sawing, chipping and otherwise shaping tissue and bone. Large suction tubing cannot be tolerated in this environment where suction is deemed to be a more secondary consideration in the surgery. Also, the suction tubing is often placed into confined tissue cavities to remove liquid and solid debris. Larger diameter suction tips and tubing cannot access these areas. Suction tubing with a diameter larger than ⅝ inch is generally perceived to occupy too much of the limited space available at the surgical site.

A further requirement of suction at an orthopedic surgical site is that it have a sufficient inside diameter to accommodate the largest solid particles. As previously noted, bone chips as large as ¼ inch may require removal from the surgical site. In this case the inside diameter of the suction tubing must be greater than ¼ inch.

A suction conduit is illustrated in FIG. 1 and designated generally by the reference numeral 10. The conduit 10 is coupled through a liquid containment vessel 12 to a source of suction, which in a preferred embodiment includes a smoke evacuator 14.

In the illustrated embodiment, the conduit 10 extends between a distal end 18 and a proximal end 21 which is connected to the containment vessel 12. A distal section 23 of the conduit 10 includes a flexible tube 25 which is coupled through a connector 27 to a rigid handpiece 30 which is located at the distal end 18 of the conduit 10.

A proximal section 34 of the conduit 10 includes a tube 32 which is connected through a coupler 36 to the tube 25 in the distal section 23. The tube 32 is also coupled to the containment vessel 12 at the proximal end 21 of the conduit 10. The tube 32 preferably has a length between six and ten feet which enables the portable smoke evacuator 16 to be located at some remote distance from the operative site 41. It is the source of suction 14, as well as the tube 25 and handpiece 30, which are of particular interest to the present invention.

This suction system is particularly adapted for use in removing complex surgical fluids and debris from an operative site. In the illustrated embodiment, surgery is being performed at an operative site 41 which includes the hip 43 of a patient 45. A retractor 47 and grasper 50 are illustrated to emphasize the crowded conditions at the site 41, but otherwise form no part of the present invention. Other instruments such as electrocautery handpieces, scalpels, irrigators and sponges may also be present at the site 41. Of particular interest at the site 41 is a waste slurry 52 which might include water, saline, blood, bone adhesive, and solid particles such as bone chips 54.

A table is designated generally by the reference numeral 61 in FIG. 2. This table 61 is a plot of the velocity of air given the inside diameter of the tubing and the volume of air moving through the tubing. The velocity is tabulated in miles per hour with the inside diameter shown in inches and the volume in cubic feet per minute. The volume of air which can be moved through the tube is largely dependent upon the power of the source of suction 14. As a result, the higher the power the greater the velocity of flow for a given diameter of tubing.

Figure 3:
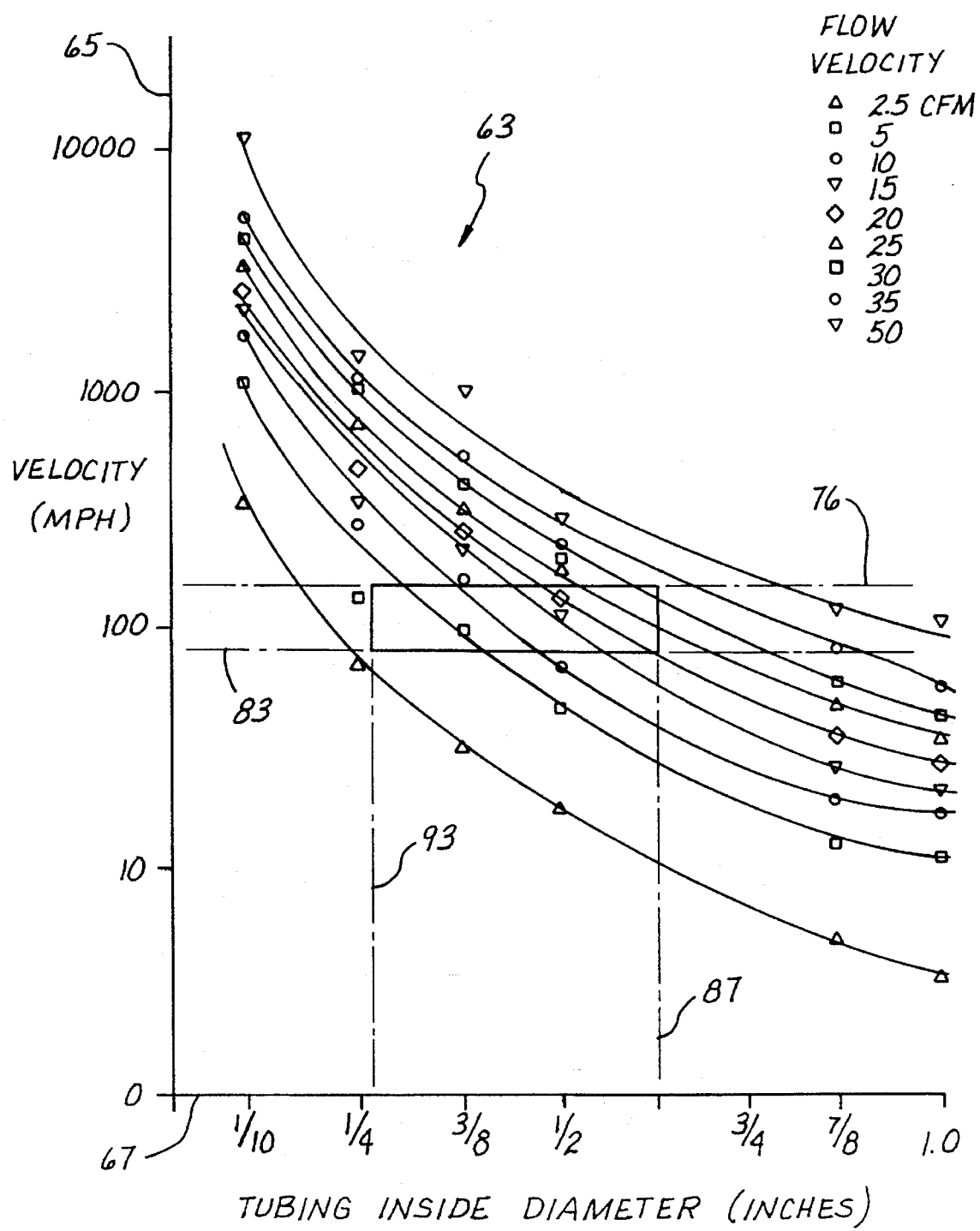
FIG. 3 is a graph plotting the velocity values tabulated in FIG. 2 for various flow volumes.

The individual velocities tabulated in Table 61 are also plotted in a graph illustrated in FIG. 3 and designated generally by the reference numeral 63. The graph 63 is a plot of velocity against the inside diameter of the tube for various volumes of flow. Velocity is plotted in miles per hour along an ordinate 65 of the graph 63, while the inside diameter is plotted in inches along an abscissa 67 of the graph 63.

Both the table 61 and the graph 63 are highly theoretical and in no way consider the friction forces and resulting loss of pressure which develop in the smaller diameters. This criteria alone makes it impossible to develop some of the higher velocities shown on the table 61 for the smaller tubing diameters and volumes. These theoretical velocities which are not capable of being achieved, given the more practical considerations of friction, are intralineated with lines, such as the line 70 (FIG. 2), which pass with a positive slope from left to right. These numbers all fall to the left of a dividing line 74 in the table 61 and above a dividing line 76 in the graph 63. The velocities which can be realistically achieved are tabulated to the right of the line 74 in table 61 and below the line 76 in the graph 63.

Of these velocities which realistically can be achieved, many are of a magnitude which is too low to accommodate the waste slurry 52 of interest to the present invention. As noted, a velocity of at least ninety miles per hour must be achieved in order to effectively move the slurry 52 into the conduit 10. In the table 61, the velocities below ninety miles per hour are intralineated with lines, such as the line 78, which have a downward slope from left to right. These numbers fall to the right of a dividing line 81 in the table 61, and below a dividing line 83 in the graph 63.

It follows that the velocities of interest in the present invention are those velocities over ninety miles per hour which can be realistically achieved. The numbers tabulated in FIG. 2 which meet this criteria fall between the lines 74 and 81 in the table 61, and between the lines 76 and 83 in the graph 63.

Two other criteria are established for a preferred embodiment of this system which is specifically adapted to the waste slurry 52. Each of these criteria have to do with the size of the tubing associated with the distal section 23. For the reasons previously established, this tubing should not exceed a diameter of 5/8 inch in order that the handpiece 30 might not occupy too much of the limited space available at the site 41. The velocities associated with these diameters which are too large, are shown to the right of a dividing line 85 in the table 61 and to the right of a dividing line 87 in the graph 63. In the table 61, these additional velocities are intralineated with the crossed lines such as those designated by the reference numeral 90.

It was also noted that the inside diameter of the tubing in the distal section 23 should not be less than 1/4 inch in order that it might accommodated the waste slurry 52 having bone chips 54 as large as 1/4 inch. Of course this criteria will vary widely with the specific configuration of the waste slurry 52. The velocities associated with this tubing which is too small, are tabulated to the left of a dividing line 92 in FIG. 2 and a dividing line 93 in FIG. 3. In the table 61, these additional velocities are intralineated with a horizontal line such as the line 96.

Given the four criteria initially set forth for the preferred embodiment, it is apparent that very few combinations of tubing size and suction power provide the required velocity. Referring specifically to the table 61, a tubing size with an inside diameter of 3/8 inch will provide a velocity at 100 miles per hour if the source of suction 14 is capable of providing suction at the rate of five cubic feet per minute. Tubing having an inside diameter of 1/2 inch can provide velocities greater than ninety miles per hour if the source of suction 14 has sufficient power to move 15 or 20 cubic feet per minute. In the table 61, these velocities are bounded by the dividing lines 74, 81, 85 and 92.

In the graph 63, these same velocities are included within the boundaries established by the dividing lines 76, 83, 87 and 93. Only within the perimeter established by these lines, is the inside diameter of the tube greater than a 1/4 inch, the outside diameter of the tube not greater than 5/8 inch, the velocity greater than ninety miles per hour and the suction power within the capacity of that commonly available in an operating room.

One other consideration is worthy of note, and that is the length of the tubing forming the distal section 23. This includes the length of the tube 25 as well as the handpiece 30. As the length of the tube increases, so does its resistance to flow. It has been found that if the tubing in the distal section 23 is maintained to a length of less than four feet, then the numbers set forth in the table 61 and plotted in the graph 63 are achievable. Beyond that length, the velocity figures tend to fall off due to excessive friction in the tube.

Since it is unrealistic to expect that the smoke evacuator 14 could be positioned only four feet from the site 41, the tube 32 in the proximal section 34 is relied on to provide additional separation. This tube 32 in a preferred embodiment has an inside diameter of ⅞ inch. While this would be too large for the surgical site 41, it is not constrained by that criteria if it is disposed proximally of the four foot section 23. Although the velocity within the larger tube 32 will be less than that in the tube 25, and probably less than ninety miles per hour, flow of the slurry 52 within the proximal section 34 can be facilitated by elevating the tube 32 so that gravity can assist in movement of the slurry 52 toward the containment vessel 12.

Figure 4:
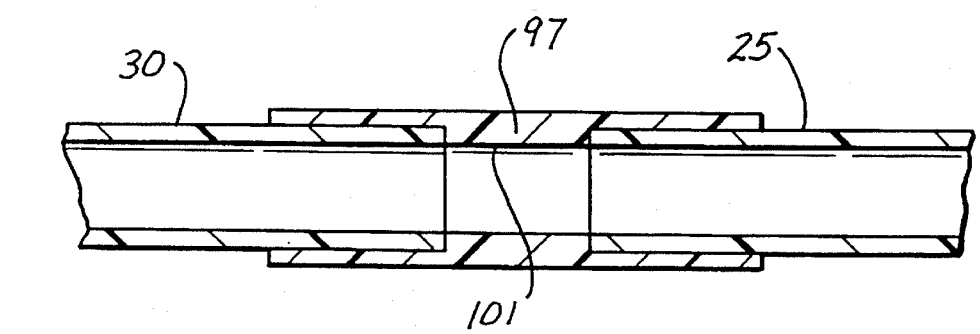
FIG. 4 is an axial cross-section view of a cylindrical tubing coupler associated with the present invention.

Since turbulent flow generally degrades the velocity of the suction fluid, a preferred embodiment insures that the connectors 27 and 36 are provided with an inside surface which smoothly transitions between the inside diameters of the respective tubes. Thus the connector 27 in FIG. 4 can be provided with a central annular flange 97 having a cylindrical inner surface 101 with an inside diameter corresponding to that of the handpiece 30 and the tube 25.

Figure 5:
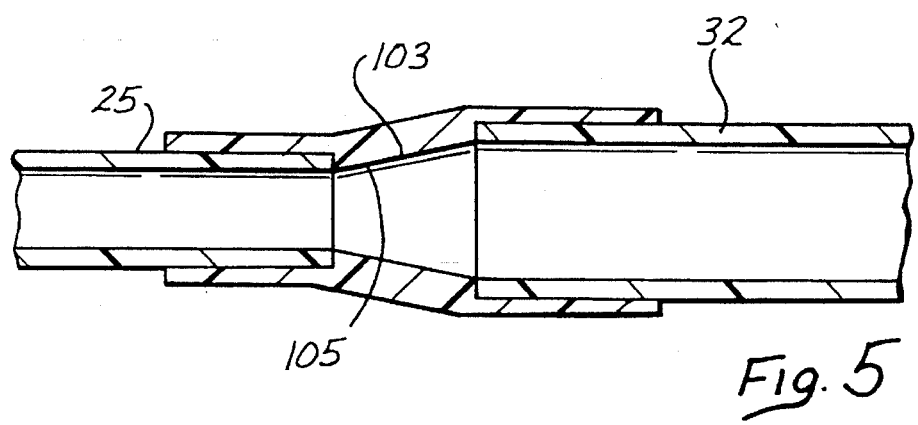
FIG. 5 is an axial cross-section view of a conical tubing coupler associated with the present invention.

The connector 36 illustrated in FIG. 5 can be provided with a central flange 103 having an inside surface 105 with a conical configuration providing a transition between the inside diameter of the tube 25 and the tube 32.

As one contemplates the power necessary to produce suction with a required magnitude, there is certainly a possibility that the source of suction 14 could be designed and manufactured for just this application. However, the limited space available in an operating room is jealously guarded and must be shared with other important systems. While wall vacuum must be considered, it simply does not have the capacity to provide the necessary power to the system.

The only other source of suction commonly available in an operating room is not designed or intended for use in suctioning liquids, let alone solids. Nevertheless, these surgical smoke evacuators are available with sufficient power to provide the suction velocities required for the waste slurry 52.

As with any system involving simple measurements, an infinite variety of embodiments are possible. Certainly any tubing having an inside diameter greater than the size of solid particles in the slurry 52 is of interest. In the most preferred embodiment where the particle size is deemed not to exceed ¼ inch, the tubing can have any inside diameter greater than a ¼ inch. But the tubing must also have an outside diameter sufficiently small to fit within a surgical environment. In the preferred embodiment, tubing having a diameter greater than ⅝ inch is considered to be inappropriate. Also, any length of tubing that will permit the desired velocity sufficient to move the slurry 52 is applicable to this concept. In a preferred embodiment, a velocity of ninety miles per hour is deemed to be necessary. Where sufficient suction power is available, higher velocities can be achieved. However these velocities must be tempered by the tendency of any such system to suck surrounding tissue and other unwanted objects into the suction system.

With the wide variations of structure applicable to the present concept, one is cautioned not to determine the scope of the invention merely by reference to the disclosed embodiments, but rather with careful consideration of the scope of the following claims.

We claim:

1. A method for evacuating a waste slurry from an orthopedic surgical site, the slurry including blood clots and bone fragments, the method comprising the steps of:

providing a source of suction;

providing a conduit with a proximal end and a distal end, the conduit at the distal end having an outside diameter not greater than about ⅝ inches in order to provide limited access to the surgical site, and an inside diameter not less than about ¼ inch to accommodate the bone fragments in the waste slurry;

connecting the proximal end of the conduit to receive suction from the suction source;

activating the source of suction to provide suction at the distal end of the conduit, the suction having a velocity of not less than ninety miles per hour;

moving the waste slurry, including blood clots and bone fragments, into the distal end of the conduit, having the outside diameter not greater than about ⅝ inches in order to provide limited access to the surgical site and having the inside diameter not less than about ¼ inch to accommodate the bone fragments in the waste slurry, and through the conduit toward the suction source; and collecting the waste slurry in a fluid containment vessel.

2. The method recited in claim 1 wherein the step of providing the conduit includes the steps of:

providing the conduit with a tube section having an inside diameter in a range between about ¼ inch and about ½ inch; and positioning the tube section at the distal end of the conduit.

3. The method recited in claim 2 wherein the step of providing the tube section includes the step of limiting the tube section to a length not greater than about four feet.

4. The method recited in claim 2 wherein the step of providing the tube section includes the step of limiting the inside diameter of the tube section to the not more than about ⅜ inch.

5. A surgical suction system adapted for use in removing a waste slurry from an orthopedic surgical site, the waste slurry including blood clots and bone fragments, and the system comprising:

a conduit having a proximal end and a distal end, the conduit having at its distal end an outside diameter not greater than about ⅝ inch and an inside diameter not less than about ¼ inch;

a suction means for providing suction at the distal end of the conduit when the proximal end of the conduit is coupled to the suction means, the provided suction having velocity at the distal end of the conduit not less than ninety miles per hour in order to draw the waste slurry at the surgical site into the distal end of the conduit;

means for coupling the proximal end of the conduit to the suction means;

a liquid trap included in the means for coupling and being disposed between the proximal end of the conduit and the suction means, the liquid trap having a volume sufficient to collect the waste slurry, including blood clots and bone fragments, passing along the conduit.

6. The system recited in claim 5 wherein the conduit comprises a tube section disposed at the distal end of the conduit, the tube section having an inside diameter in a range between about ¼ inch and about ½ inch.

7. The system recited in claim 6 wherein the inside diameter of the tube section is about ⅜ inch.

8. The system recited in claim 6 wherein the tube section has a length not greater than about four feet.

* * * * *